(12) United States Patent
Power

(10) Patent No.: US 6,221,080 B1
(45) Date of Patent: Apr. 24, 2001

(54) BIFURCATION LESION STENTING CATHETER

(76) Inventor: John A. Power, 202 Springhouse La., Pittsburgh, PA (US) 15238

(*) Notice: Subject to any disclaimer, the term of this patent is extended or adjusted under 35 U.S.C. 154(b) by 0 days.

(21) Appl. No.: 09/458,371

(22) Filed: Dec. 10, 1999

(51) Int. Cl.$^7$ .................................................. A61F 11/00
(52) U.S. Cl. ........................................... 606/108; 606/195
(58) Field of Search .................................... 606/108, 198, 606/191, 192, 195, 113, 1; 128/898; 604/104; 623/1.15

(56) References Cited

U.S. PATENT DOCUMENTS

| | | |
|---|---|---|
| 4,681,110 | 7/1987 | Wiktor . |
| 4,886,062 | 12/1989 | Wiktor . |
| 4,913,142 | 4/1990 | Kittrell et al. . |
| 4,969,458 | 11/1990 | Wiktor . |
| 5,133,732 | 7/1992 | Wiktor . |
| 5,217,454 | 6/1993 | Rhoury . |
| 5,437,659 | 8/1995 | Leckronte . |
| 5,575,816 | 11/1996 | Rudnick . |
| 5,669,932 | 9/1997 | Fischell . |
| 5,722,972 | 3/1998 | Power . |
| 5,749,825 * | 5/1998 | Fischell et al. ........................ 606/194 |
| 5,772,669 * | 6/1998 | Vrba ..................................... 606/108 |
| 5,776,101 * | 7/1998 | Goy ....................................... 606/192 |
| 6,048,361 * | 4/2000 | Von Oepen ........................... 606/108 |
| 6,056,775 * | 5/2000 | Borghi et al. ........................ 606/195 |
| 6,117,156 * | 9/2000 | Richter et al. ....................... 606/194 |

\* cited by examiner

*Primary Examiner*—Pedro Philogene
(74) *Attorney, Agent, or Firm*—Clifford A. Poff

(57) ABSTRACT

A stent deployment catheter includes a catheter body extending to an elongated distal end portion adapted for supporting and deploying a stent having a cylindrically shaped sidewall expandable in a vessel lumen to treat lesions. The distal end portion bearing the stent is guided within vessel lumen to a site therein to treat the lesions. Two guide wires are placed one in each of the bifurcations of a branched vessel. A guide wire lumen in the catheter is used to direct the elongated distal end portion along the guide wire to a vessel branch containing the lesions and a side branch guide wire lumen protectively isolates a length of a side branch guide wire from the stent when supported by the elongated distal end portion to establish a predetermined deployment site for a distal end portion and a proximal end portion of the stent for treating lesions of the first branch. The side branch guide wire lumen extends along the elongated distal end portion of the catheter to establish a predetermined side branch guide wire entry port within the extended length of the elongated distal end portion of the catheter for receiving a side branch guide wire after radially permeating the sidewall of the stent when carried by the distal end portion. After the catheter and guide wire are removed from the vessel branch, the side branch guide wire is used to treat lesions in the side branch by guiding a catheter through struts of the deployed stent.

15 Claims, 6 Drawing Sheets

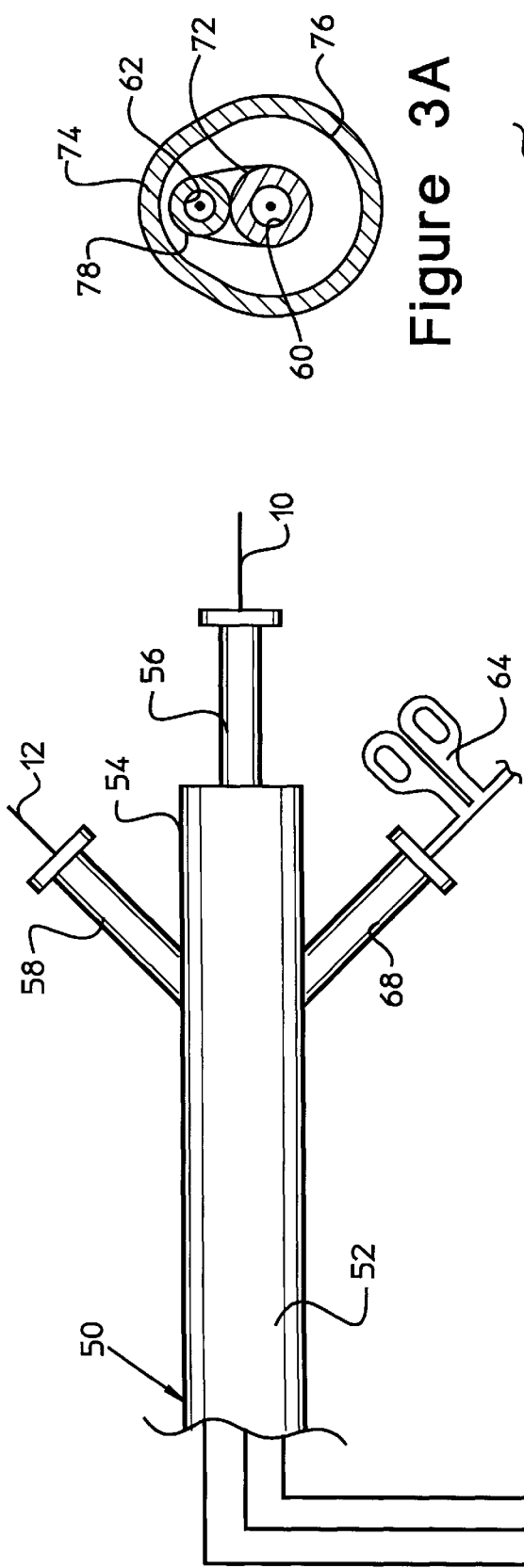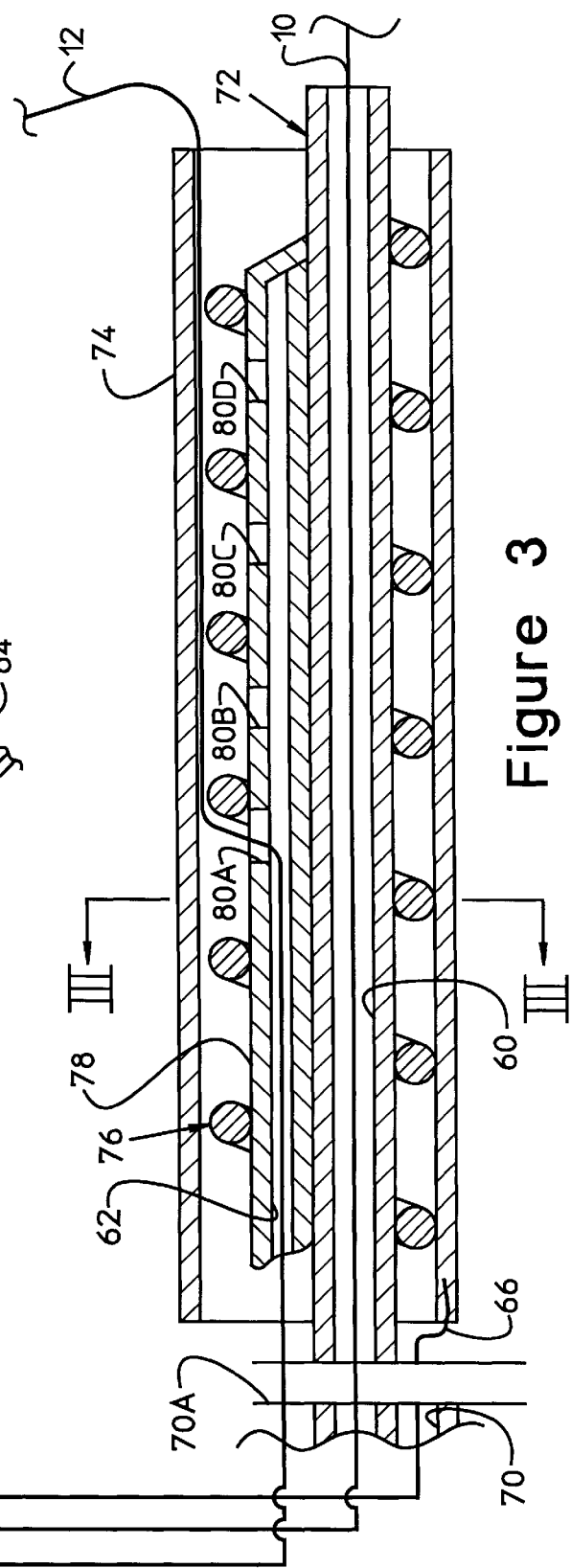
Figure 3
Figure 3A

BIFURCATION LESION STENTING CATHETER

CROSS REFERENCE TO RELATED APPLICATION

Not applicable.

BACKGROUND OF THE INVENTION

1. Field of the Invention

The present invention relates to a catheter for transporting and deploying a stent to treat bifurcation lesions in a branching anatomic duct, and more particularly, to such a catheter having a distal end portion including a catheter body extending to an elongated distal end portion for carrying a stent while guided along a vessel lumen by one of two guide wires a first of which extends to a first branching duct having bifurcation lesions to be treated and the other of the guide wires penetrates a wall of the stent to establish a predetermined distal end portion and predetermined proximal end portion of the stent advanced only along the first guide wire to treat bifurcation lesions of the first branching duct.

2. Description of the Prior Art

Angioplasty is a well-known procedure used to treat atherosclerosis involving the use of a balloon-tipped catheter to treat a narrowed anatomic duct such as a coronary artery. The balloon mounted on the distal end of a catheter is advanced to the narrowed opening in the artery and then the balloon is expanded one or more times to compress arterial plaque and enlarge the narrowed opening. Anatomic ducts treated by angioplasty however can re-close within a short time (referred to as acute re-closure) or again assume a re-narrowing over extended period (referred to as re-stenosis).

Stenting is a technique used to open blocked arteries in patients who have atherosclerosis. The blocked arteries can affect any organ system in the body but are most frequently approached with stenting when the lesion or blockage affects an artery supplying fluid to the heart, brain, kidney or legs.

The installation of a stent initially follows the same procedure involved in an angioplasty of placing a guide-wire across the blockage in the artery and then using the guide wire to advance a balloon dilatation catheter to the site of the blockage whereupon the balloon is inflated to compress plaque and dilate the blockage. A selected stent arranged on a dilation balloon is then advanced along the artery with the aid of the guide wire to a position where stent traverses the site of the blockage. The balloon is inflated to permanently enlarge the stent against the wall of the artery leaving the stent anchored in place. After deflating the balloon and removing of the catheter, the guide wire is removed completing the stent installation procedure. The stent serves as a prop in the artery to help prevent both acute re-closure and to maintain vessel dilation of the treated area of the blood vessel to prevent re-stenosis.

Although stenting a blood vessel is preferred to plain balloon angioplasty in most circumstances, many anatomical situations make it very challenging or impossible to deploy a stent safely. Bifurcation lesion, tortuous blood vessels, ostial lesions and calcified blood vessels are just a few of the very challenging anatomical situations.

Bifurcation lesions are blockages occurring at a branch point of the blood vessel. When only one guide-wire is placed down the blood vessel and used to dilate the vessel at the bifurcation lesion, it is likely that the atherosclerotic material will be forced into the branch of the blood vessel which does not contain the guide-wire and balloon resulting in closing off the unaccessed branch of the blood vessel. This can result in severe damage to the organ supplied with blood by the blood vessel causing a heart attack if the blood circulation is supplied to the heart or a stroke if the blood circulation is supplied to the brain. It is known to simultaneously place a guide-wire down each branch simultaneously and then dilate each branch of a branch duct with a balloon either simultaneously or in at very closely spaced intervals. As long as a guide-wire is maintained across a branch with bifurcation lesions, a balloon catheter can be advanced into that branch even if some previously dilated material from the other branch is squeezed into the branch with lesions. The guide-wire serves as a reliable track providing a pathway for delivering a distal end of a catheter to the branch with lesions at a later point in time. However, it is frequently impossible to place a guide-wire along a side-branch that has been closed-off and, for this reason, two guide-wires are used for treating a bifurcation lesion of a bifurcation vessel.

In the event a stent is advanced into a bifircation lesion after both branches have been dilated, the guide-wire not used for placement the stent must be removed because the guide-wire will become permanently trapped in the wall of the blood vessel when the stent is deployed. However, as pointed out earlier, if the second guide-wire not used for stenting is removed and the stent is deployed using the first guide wire, some of the residue of the atherosclerotic material can be squeezed into the side branch and create a blockage. Even if such a blockage does not occur, maneuvering a guide-wire into the blocked side-branch is difficult because the guide-wire has a tendency to impact and deflect in an unpredictable manner with the struts of the stent adversely affecting steering of the guide wire. The possibility of using a Y-shaped stent was suggested for treating a bifurcation lesion but this stent configuration has an increased bulk adversely affecting upon the success to advance a catheter bearing the stent along a blood vessel to the desired stent deployment site.

Another difficult blockage to approach with a stent is the ostial lesion. This is a blockage occurring at the opening of the blood vessel. Stent deployment has been more successful for treating ostial lesions but still remains challenging because the stent must not overhang in the adjoining vessel and the stent will be of little value if it is placed too far in the vessel obstructed by the ostial lesion. Once a stent is deployed, moving it is impossible.

There are many other anatomic considerations which make stent placement difficult. Tortuous blood vessels are those which have many curves. Stents have a certain degree of stiffness and are sometimes not sufficiently flexible to advance along a course having a very tight curve or multiple soft curves. Other anatomic considerations are calcified blockages which have the characteristic of accumulated calcium in the wall of the blood vessel imparting a very hard bone like physical characteristic to the blood vessel. A calcified blood vessel is difficult or impossible to dilate and treat by balloon angioplasty because of the possibility of tearing of the vessel wall as a result of the increased force needed to dilate the calcified blockage.

It is an object of the present invention to provide safer deployment of a stent for treating bifurcation lesions, tortuous blood vessels, ostial lesions and calcified blood vessels.

It is a further object of the present invention to provide a stent deployment catheter to allow safer and more accurate stent deployment at a predetermined site relative to bifurcation lesions and ostial lesions.

It is another object of the present invention to provide a stent deployment catheter embodying a design and construction of parts to allow the use of one of two guide wires for establishing a length of a distal end portion of a stent for treating a blockage traversed and protectively isolated by the other of the guide wires.

SUMMARY OF THE INVENTION

According to the present invention there is provided a stent deployment catheter for a stent having a cylindrically shaped sidewall to treat lesions, the stent deployment catheter including: a catheter body extending to an elongated distal end portion adapted for supporting and deploying the stent to be inserted into and guided within vessel lumen to a site therein to treat lesions, a guide wire lumen to direct the elongated distal end portion along a guide wire to a branch containing lesions, and a side branch guide wire lumen protectively isolating a length of a side branch guide wire from the stent when supported by the elongated distal end portion to establish a predetermined deployment site for a distal end portion and a proximal end portion of the stent for treating lesions of the first branch, the side branch guide wire lumen extending along the elongated distal end portion to establish a predetermined side branch guide wire entry port within the. extended length of the elongated distal end portion for receiving a side branch guide wire after radially permeating the sidewall of the stent when carried by the distal end portion.

According to the present invention there is also provided a method for treating lesions, the method including the steps of advancing a first guide wire along the vessel through a first branch containing lesions, advancing a second guide wire along the vessel through a second branch containing lesions, mounting a stent on an elongated distal end portion of a stent deployment catheter, introducing the first guide wire to an internal guide wire lumen extending wholly interiorly of the elongated distal end portion toward a proximal end of the stent deployment catheter, establishing a predetermined distal end portion of the stent to treat lesions traversed by the first guide wire by introducing the second guide wire through a cylindrical wall of a stent at a predetermined site within the distal end portion to an entry port of a guide wire lumen segment interior of essentially only a remaining proximal end portion of the stent, advancing the distal end portion and a stent supported thereby along the first and second guide wires to introduce the predetermined distal end portion of the stent to lesions of the first branch, deploying the stent from the distal end portion, withdrawing the distal end portion of the stent deploying catheter and the first guide wire, and using the second guide wire to treat lesions of the second branch.

BRIEF DESCRIPTION OF THE SEVERAL VIEWS OF THE DRAWINGS

These features and advantages of the present as well as others will be more fully understood when the following description is read in light of the accompanying drawings in which:

FIG. 2A is a sectional view taken along lines II—II of FIG. 2;

FIG. 3 is a view similar to FIG. 2 and illustrating the distal end portion of a stent deployment catheter according to a second embodiment of the present invention;

FIG. 3A is a section view taken along lines III—III of FIG. 3;

DETAILED DESCRIPTION OF THE PREFERRED EMBODIMENTS

Figure 1:
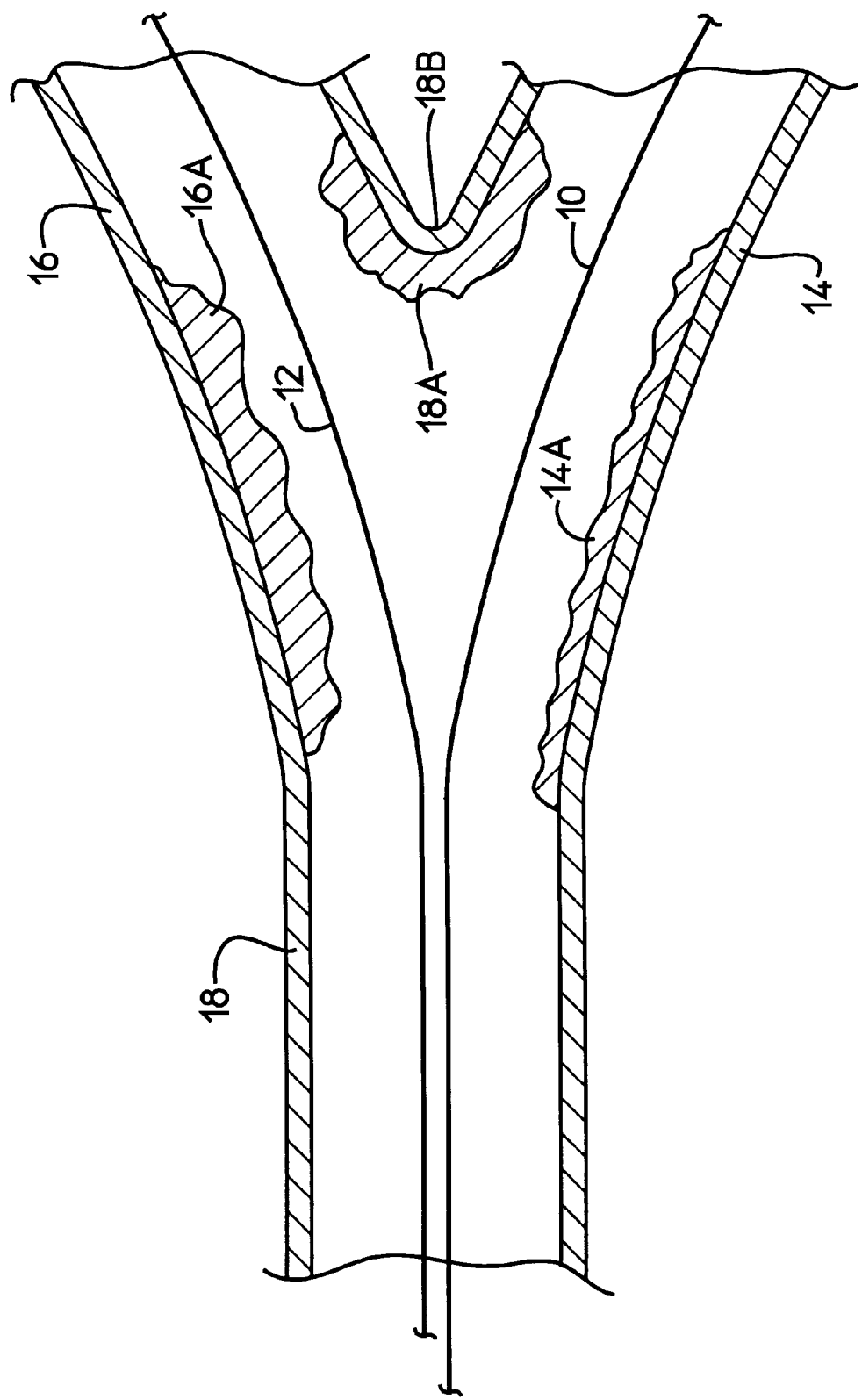
FIG. 1 illustrates an example of a bifurcation lesion wired with two wires and dilated with a conventional balloon dilatation catheter.

As shown in FIG. 1, the lesion stenting catheter of the present invention will be described for use with two guide wires 10 and 12 for treating bifurcation lesions that impair fluid flow in vessel branches 14 and 16 of a vessel 18. As will be apparent to one skilled in the art the lesion stenting catheter is useful for treating torturous blood vessel ostial lesions and calcified blood vessels. Bifurcation lesions are diagrammatically depicted as deposits of atherosclerotic plaque at sites which are identified by reference numerals 14A and 16A extending along the outer vessel walls of branches 14 and 16, respectively. Other sites of atherosclerotic plaque is identified by reference numeral 18A extending along the two diverging walls of vessel 18 from the site of crux 18B. The bifurcation lesion is initially addressed by the placement of the two guide wires 10 and 12 along the vessel and extending across the vessel branches 14 and 16. After placement of the guide wires, the branches 14 and 16 are dilated with a balloon dilatation catheter using standard angioplasty procedure. A stent deployment catheter is then selected. According to the present invention two embodiments are provided, one embodiment, shown in FIG. 2 includes a balloon to deploy a stent and a second embodiment, shown in FIG. 3, includes a retractable sheeting to deploy a self-expanding stent.

Figure 2:
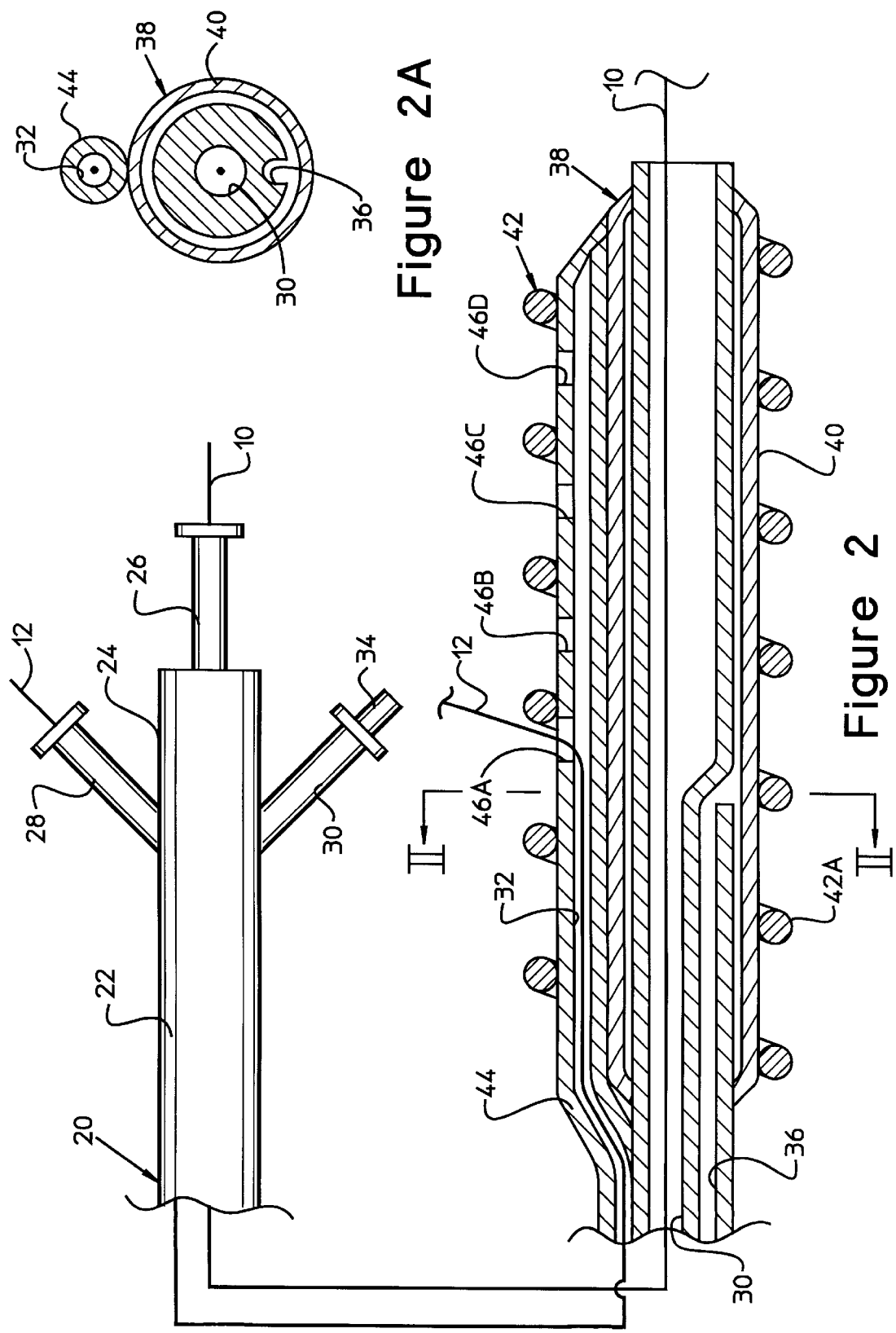
FIG. 2 is an enlarged view in section illustrating the distal end portion of a stent deployment catheter according to one embodiment of the present invention.

As shown in FIGS. 2 and 2A, the stent deployment catheter 20 includes a catheter body 22 having a proximal end portion 24 provided with connectors 26 and 28 communicating with guide wire lumens 30 and 32, respectively, to allow passage of the guide wires 10 and 12 exteriorly of the proximal end portion 24 of the catheter. A connector 34 is provided to connect with a syringe for introducing an inflation medium to a lumen 36 extending to an elongated distal end portion 38 and communicating with an annular cavity formed by an overlying and expandable inflation balloon 40. The balloon envelops an elongated periphery of the elongated distal end portion. The distal end portion 38 and inflation balloon 40 together form a stent carrier of a sufficient length and diameter to support a stent 42 having radially expandable struts 42A supported in an unexpanded state about the outer surface of the inflation balloon 40. Examples of radially expandable stents are disclosed in U.S. Pat. Nos. 4,886,062; 5,133,732; and 5,575,816. A tubular segment 44 is adhered or otherwise mounted on the exterior of the inflation balloon to provide a protectively isolated pathway for the guide wire 12 which enters the tubular segment 44 through one of a plurality of spaced apart guide wire entry ports 46A, 46B, 46C and 46D. A particular guide wire entry port is selected to establish an ideal location for the deployed stent so that a predetermined length of a distal end portion of a stent resides in the main branch 14 and a predetermined length of a proximal end portion of the stent resides in vessel 18. For example, when guide wire entry port 46D is chosen, then the predetermined distal end portion of the stent is shorter as compared with the length of a distal end portion formed by selecting the guide wire exit port 46A. It is now apparent that the guide wire 12 must exit the distal end of the stenting catheter within length of the distal end of the stent which is to reside in the main branch 14 of vessel 18. The tubular segment 44 preferably extends in a generally parallel relation with elongated distal end portion 38, however, other nonparallel relations may be used without departing from the present invention.

Shown in FIGS. 3 and 3A is a second embodiment of stent deployment catheter 50 which includes a catheter body 52 having a proximal end portion 54 provided with connectors 56 and 58 communicating with guide wire lumens 60 and 62, respectively, to allow passage of the guide wires 10 and 12 exteriorly of the catheter. A handle 64 connected to an actuator wire 66 emerging from the proximal end portion 54 at a connector 68 for pulling on the actuator wire 66 in order to activate it. The actuator wire 66 is protectively housed in a lumen 70 extending to an elongated distal end portion 72 where the actuator wire is connected to a sheathing 74. The sheathing envelopes a self-expanding stent 76 to maintain the stent in an unexpanded condition and in a state of readiness for expansion upon removal of the sheathing. The stent 76 is mounted on the elongated distal end portion 72 which together form a stent carrier of a sufficient length and diameter to support the self-expandable stent 76 in an unexpanded state. An example of a self expandable stent is disclosed in U.S. Pat. No. 4,681,110. A tubular segment 78 is adhered exteriorly to the elongated distal end portion 72 to provide a pathway for the entrance of guide wire 12 through one of a plurality of spaced apart guide wire entry ports 80A, 80B, 80C and 80D. These guide wire ports serve the same function as ports 46A, 46B, 46C and 46D. It will be observed from FIG. 3 that the guide wire extends along a distal end portion of the sheathing 74 to the entry site of an entry port and then extends internally of the tubular segment. The tubular segment 78 extends generally parallel with elongated distal end portion 72. The sheathing 74 is displaced by the actuator wire 66 along the distal end portion in the direction of the extended length toward the proximal end portion by operation of handle 64. The lumen 70 terminates at a site generally denoted by reference numeral 70A which is spaced from the proximal end of the sheathing by a distance slightly greater than the extending length of the sheathing to provide a storage site for the sheathing when displaced toward the proximal end of the catheter. The force is imparted to the sheathing 74 by the operation of actuating wire 66 are sufficient to remove the constraint placed on the stent by the sheathing and thereby allow the self-expanding property of the stent to cause expansion and placement of the stent at the intended site as determined by the location of the distal end portion in the branching vessel.

Figure 4:
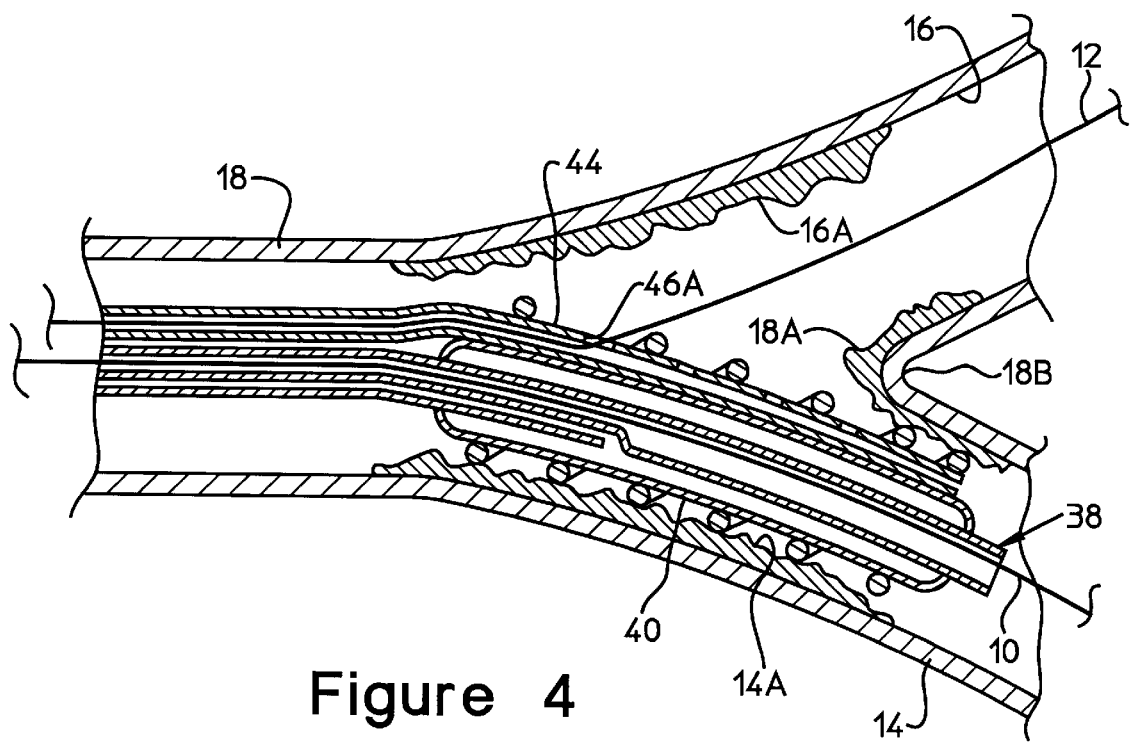
FIGS. 4–8 illustrate sequence of placement of a stent by a stent deployment catheter of the present invention includ-ing the presences of two guide wires placed along bifurcation branches containing bifurcation lesions.
Figure 5:
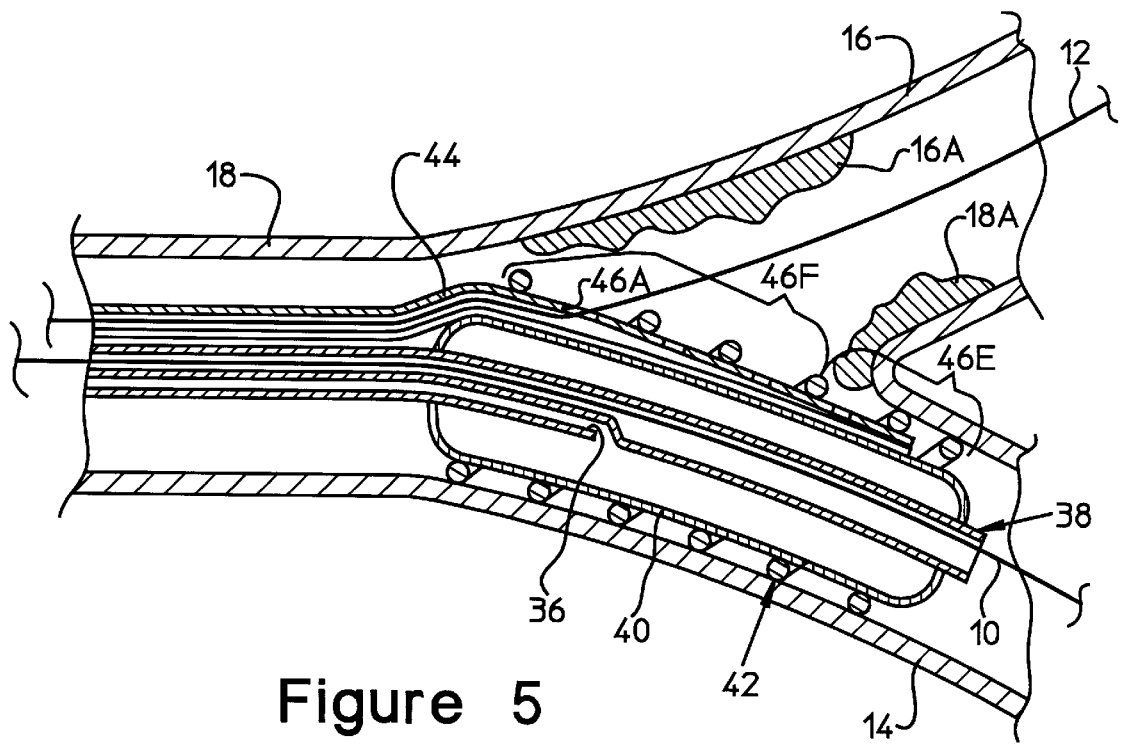

The operation of the catheter according to the present invention is illustrated in FIGS. 4–8 and follows the placement of the guide wires 10 and 12 in the vessel branches 14 and 16 of the vessel 18 and treatment of the bifurcation lesions using standard angioplasty procedure using in succession the guide wires 10 and 12. The stenting of the bifurcation lesions using a stent deployment catheter according to the embodiment of FIG. 2 will now be reference for the purpose of the detailed description of the use of the catheter. The guide wires 10 and 12 are introduced in the distal end portion 38 of the catheter by passing the guide wire 10 along the guide wire lumen 30 to the proximal end portion 24 where the guide wire emerges from the connector 26. The guide wire 12 is inserted in a radial direction in reference to the generally tubular nature of the stent 42 between struts 42A of the stent 42 and then into a preselected one of the guide wire entry ports 46A, 46B, 46C or 46D. The selection of the guide wire entry port is chosen to establish an approximate deployment site along the branching vessel to thereby provide a desired length of the distal end portion of the stent which is to extend along the vessel branch 14 and provide the length of the proximal end portion of the stent to bridge and, if desired, reside in the main vessel 18. As shown in FIGS. 4 and 5, guide wire entry port 46A is chosen to receive the guide wire and thereby provide a distal stent portion 46E resident along vessel branch 14 and a proximal stent portion 46F traversing the branching region and partially resident in vessel 18.

Figure 6:
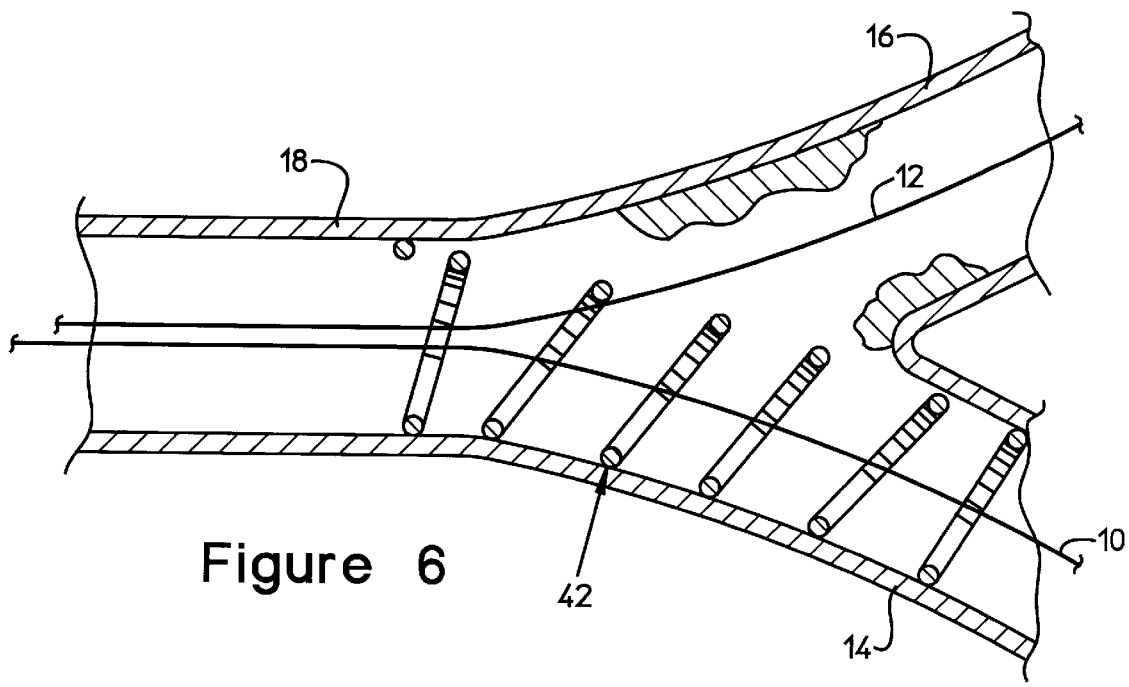
Figure 7:
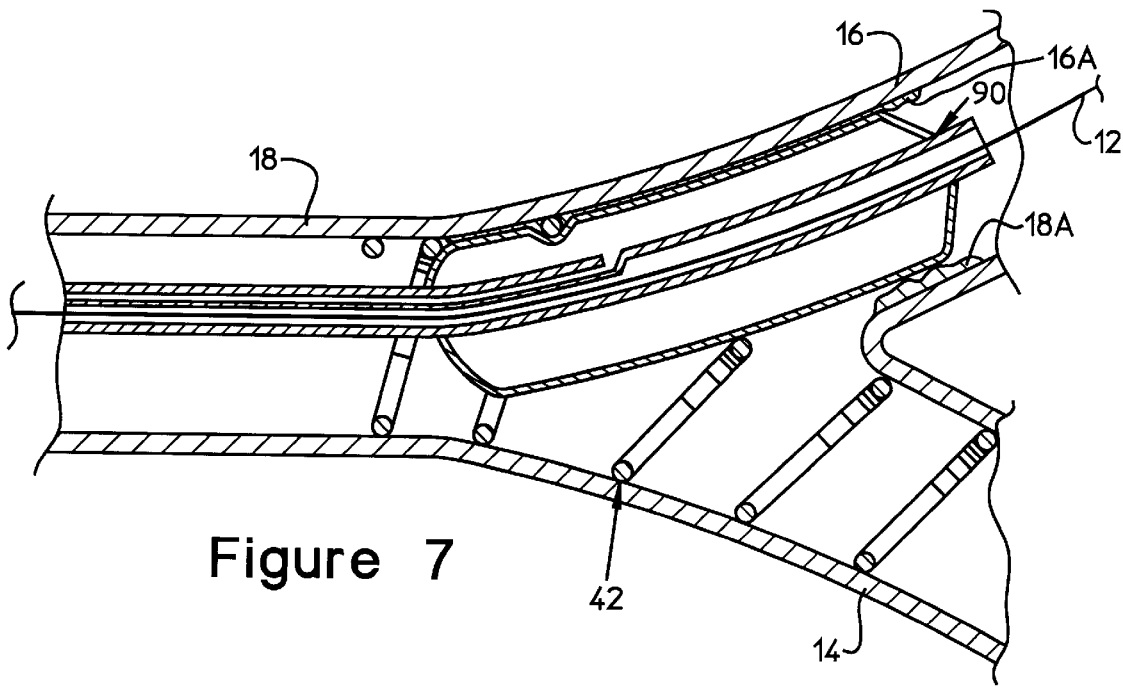
Figure 8:
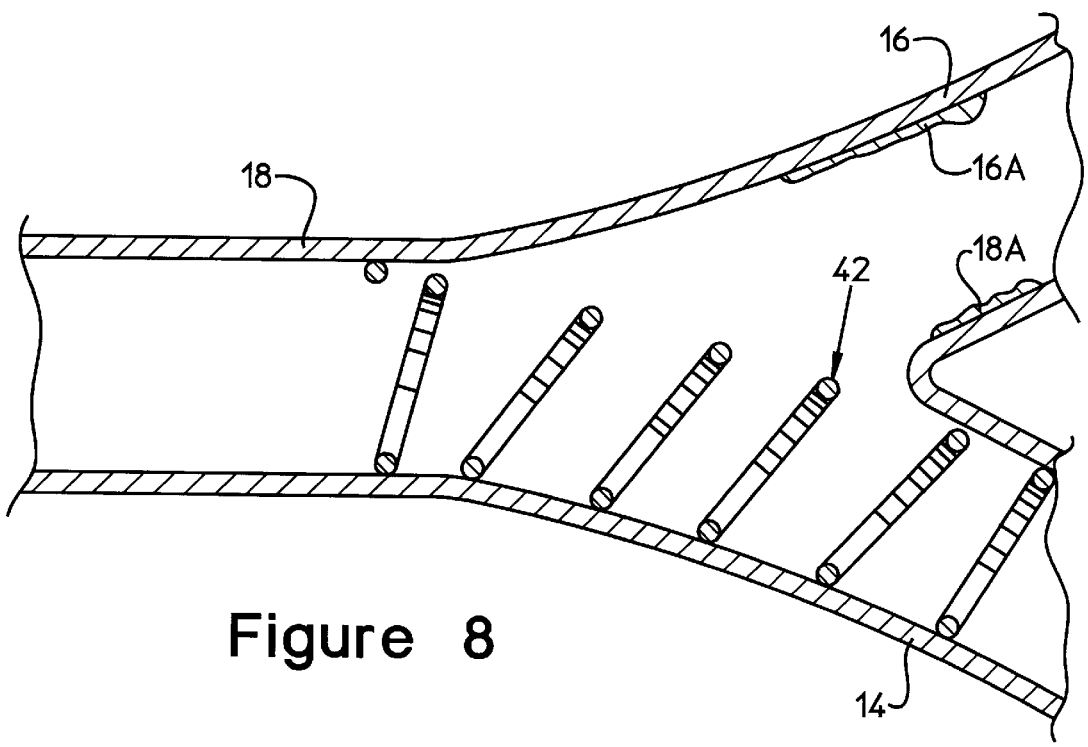

As explained hereinbefore, the present invention provides for the presence of two guide wires, one in each branch of the branching vessel used at different times for stenting bifurcation lesions of vessel branches. It is therefore important as shown in FIGS. 4 and 5 that the distal end portion of the stent intended to reside in the vessel branch 14 of the vessel 18 not entrap the guide wire 12 against the vessel wall. As shown in FIG. 6, the guide wire 12 remains effective to guide a catheter along vessel 18 and thence between struts of the proximal stent portion 46F to allow placement of a conventional balloon catheter or a stent deployment catheter on the side branch. In FIG. 7 there is illustrated the placement of a conventional balloon catheter 90 in the side branch 16, upon inflation of the balloon catheter 90, bifurcation lesions 16A and 18A are treated and produce, as shown in FIG. 8, a stented branch 14 and angioplasty treated lesions in branch 16 and vessel 18. In the event it is desired to use a self deploying stent, for treating the bifurcation lesions, the stent according to the embodiment illustrated in FIG. 3 is used to transport and deploy the stent at the intended site. The guide wires 10 and are introduced to the distal end portion 72. Guide wire 10 is introduced along guide wire lumen 60 and emerges along the catheter 66. Guide wire 12 is introduced interiorly of the sheathing 74 and passed radially through a selected one of the guide wire entry ports 80A, 80B, 80C and 80D. As in the embodiment of the catheter shown in FIG. 2 the selected guide wire entry port establishes a stent distal end portion which is to reside along the vessel branch 14 and a stent proximal end portion traversing the branching region and partly resident in vessel 18. The deployment of the stent is caused by the retraction of the sheathing as described hereinbefore in connection with the FIGS. 3 and 3A.

Figure 9:
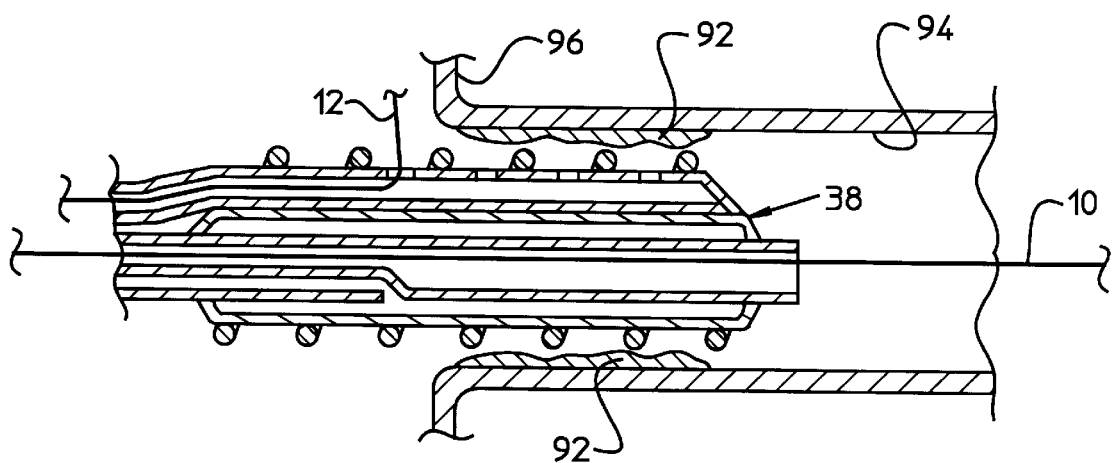
FIG. 9 is an enlarged sectional view illustrating the treatment of an ostial lesion using the stent deployment catheter according to the present invention.

FIG. 9 illustrates the use of the catheter according present invention for treating ostial lesions 92 chosen for illustration purposes only, occurring in the instance of a larger blood vessel 94 supplying a diseased blood vessel 96 treated as a side branch. The distal end portion 38 of the stent deployment catheter according to the embodiment of the present invention shown in FIG. 2 is advanced along guide wires 12 and 14 previously placed along the larger vessel 94 and side branch 96, respectively. As explained in regard to FIG. 2, the guide wire 12 is inserted in a radial direction in reference to the generally tubular nature of the stent 42 between struts 42A and then into a preselected one of the guide wire entry ports 46A, 46B, 46C or 46D. The selection of the guide wire entry port is chosen to establish an ideal location for the deployed stent along the branching vessel to thereby provide a desired length of the distal end portion of the stent which is to extend along the side branch 96 and provide the length of the proximal end portion of the stent to bridge and, if desired, reside in the larger vessel 94. The stent is deployed in a manner described hereinbefore by the introduction of a fluid medium to the lumen communicating with the inflation balloon 40.

While the present invention has been described in connection with the preferred embodiments of the various figures, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

What is claimed is:

1. A stent deployment catheter for a stent having a cylindrically shaped sidewall to treat lesions, said stent deployment catheter including: a catheter body extending to an elongated distal end portion adapted for supporting and deploying such a stent to be inserted into and guided within vessel lumen to a site therein to treat lesions; a guide wire lumen to direct said elongated distal end portion along a guide wire to a vessel branch containing lesions; and a side branch guide wire lumen protectively isolating a length of a side branch guide wire from such a stent when supported by said elongated distal end portion to establish a predetermined deployment site for a distal end portion and a proximal end portion of the stent for treating lesions, said side branch guide wire lumen extending along said elongated distal end portion and having a plurality of guide wire entry ports along the length thereof to establish a predetermined side branch guide wire entry port within the extended length of said elongated distal end portion for receiving a side branch guide wire after radially permeating the sidewall of such a stent when carried by said distal end portion said plurality guide wire entry ports selectively receiving said side branch guide wire for establishing a predetermined distal end portion and a proximal end portion of a stent when supported by said elongated end portion.

2. The stent deployment catheter according to claim 1 wherein said side branch guide wire lumen includes a tubular segment extending generally parallel with the extended length of said elongated distal end portion and terminating to form of a guide wire exit port exteriorly of said catheter body.

3. The stent deployment catheter according to claim 1 wherein said distal end portion includes an elongated stent carrier having an extended length sufficient to support a stent.

4. The stent deployment catheter according to claim 3 wherein said stent carrier includes an elongated sheathing enveloping a length of said distal end portion and sealed thereto at distal and proximate ends thereof in a fluid tight manner for forming an inflation balloon suitable to deploy a stent mounted thereon, said side branch guide wire lumen being supported exteriorly of said sheathing to reside between said balloon and a stent when supported thereby.

5. The stent deployment catheter according to claim 4 wherein said side branch guide wire lumen is secured to said elongated sheathing forming said balloon and radially displaced thereby relative to the extended length of said distal end portion.

6. The stent deployment catheter according to claim 1 wherein said stent carrier includes an elongated sheathing enveloping the cylindrical exterior of a stent when seated on said stent carrier, an actuator connected to said elongated sheathing to slide a terminal end thereof along said stent carrier in a direction of the elongated length of said sheathing to expose and allow deployment of a stent when seated on said stent carrier, said side branch guide wire lumen being supported interiorly of said elongated sheathing to reside between said stent carrier and a stent when supported by said stent carrier.

7. The stent deployment catheter according to claim 6 wherein said side branch guide wire lumen is secured to said stent carrier.

8. The stent deployment catheter according to claim 7 wherein said side branch guide wire lumen is an integral part of said stent carrier.

9. The stent deployment catheter according to claim 6 wherein said actuator includes a slide wire anchored to said elongated sheathing and extending along said catheter body to a proximal end thereof, and a control member on the proximal end of said slide wire to slide the terminal end of said elongated sheathing along said stent carrier.

10. A method for treating lesions, said method including the steps of:

advancing a first guide wire along the vessel through a first branch containing lesions;

advancing a second guide wire along the vessel through a second branch containing lesions;

mounting a stent on an elongated distal end portion of a stent deployment catheter;

introducing said first guide wire to an internal guide wire lumen extending wholly interiorly of said elongated distal end portion toward a proximal end of the stent deployment catheter;

establishing a predetermined distal end portion and proximal end portion of the stent to treat lesions traversed by said first guide wire by introducing said second guide wire through a cylindrical wall of a stent at a predetermined site within said distal end portion to an entry port of a guide wire lumen segment interior of essentially only a remaining proximal end portion of the stent;

advancing said distal end portion and a stent supported thereby along said first and second guide wires to introduce said predetermined distal end portion of the stent to lesions of said first branch;

deploying the stent from the distal end portion;

withdrawing the distal end portion of the stent deploying catheter and said first guide wire; and using said second guide wire to treat lesions of the second branch.

11. The method according to claim 10 wherein said step of deploying the stent includes expanding a stent deployment balloon arranged interiorly along the length of the stent.

12. The method according to claim 10 wherein said step of deploying the stent includes withdrawing an elongated sheathing enveloping the stent along the length thereof in a direction to expose and allow deployment of the stent then seated on the distal end portion.

13. The method according to claim 10 wherein said step of using said second guide wire to treat lesions of the second branch includes deploying a second stent from a distal end portion of a stent deployment catheter after advanced along said second guide wire to the second branch.

14. The method according to claim 10 wherein said step establishing a predetermined distal end portion of the stent to treat lesions traversed by said first guide wire includes selecting one of a plurality of entry ports in said guide wire lumen to receive said second guide wire.

15. The method according to claim 10 wherein said predetermined distal end portion of the stent is essentially only advanced along said first guide wire to lesions of said first branch by said step advancing said distal end portion and a stent supported thereby.

* * * * *